United States Patent [19]

Gruetzke et al.

[11] Patent Number: 5,633,358
[45] Date of Patent: May 27, 1997

[54] PROCESS FOR BLEACHING AQUEOUS SURFACTANT SOLUTIONS

[75] Inventors: Juergen Gruetzke, Bochum; Stefan Schmidt; Gerda Grund, both of Haltern; Uwe Tanger, Bochum, all of Germany

[73] Assignee: Huels Aktiengesellschaft, Marl, Germany

[21] Appl. No.: 527,897

[22] Filed: Sep. 14, 1995

[30] Foreign Application Priority Data

Sep. 14, 1994 [DE] Germany ............... 44 32 623.8

[51] Int. Cl.$^6$ ............... C07G 3/00; C07H 15/04; C07H 1/06
[52] U.S. Cl. ............... 536/18.5; 536/18.6; 536/124; 536/127
[58] Field of Search ............... 536/18.5, 18.6, 536/124, 127

[56] References Cited

U.S. PATENT DOCUMENTS

| | | | |
|---|---|---|---|
| 4,762,918 | 8/1988 | McDaniel, Jr. et al. | 536/124 |
| 4,904,774 | 2/1990 | McDaniel et al. | 536/127 |
| 5,206,357 | 4/1993 | Schmidt | 536/18.6 |
| 5,212,292 | 5/1993 | Ripke | 536/18.6 |
| 5,227,480 | 7/1993 | Oberholz et al. | 536/18.5 |
| 5,362,861 | 11/1994 | McCurry et al. | 536/127 |
| 5,420,262 | 5/1995 | Schmidt | 536/18.5 |
| 5,432,275 | 7/1995 | McCurry et al. | 536/120 |
| 5,461,144 | 10/1995 | Kahsnitz et al. | 536/124 |

FOREIGN PATENT DOCUMENTS

| | | |
|---|---|---|
| 0165721 | 12/1985 | European Pat. Off. . |
| 0306652 | 3/1989 | European Pat. Off. . |
| 0388857 | 9/1990 | European Pat. Off. . |
| 0526710 | 2/1993 | European Pat. Off. . |
| 4101252 | 7/1992 | Germany . |
| 4218073 | 12/1993 | Germany . |
| WO93/13113 | 7/1993 | WIPO . |

*Primary Examiner*—John Kight
*Assistant Examiner*—Everett White
*Attorney, Agent, or Firm*—Oblon, Spivak, McClelland, Maier & Neustadt, P.C.

[57] ABSTRACT

The invention relates to a process for bleaching aqueous alkyl polyglycoside solutions using hydrogen peroxide, in a first step the actual bleaching being carried out at alkaline pHs in the presence of an inorganic additive (hydrogen peroxide decomposition inhibitor) and in a second step a specific decomposition of the unreacted hydrogen peroxide being performed by contact with transition metals or inorganic compounds thereof.

10 Claims, No Drawings

PROCESS FOR BLEACHING AQUEOUS SURFACTANT SOLUTIONS

BACKGROUND OF THE INVENTION

1. Field of the Invention

The invention relates to a process for bleaching aqueous surfactant solutions using hydrogen peroxide, in a first process step the actual bleaching being carried out at alkaline pHs in the presence of inorganic additives which act as decomposition inhibitors for hydrogen peroxide and in a second process step a specific decomposition of the unreacted hydrogen peroxide and/or oxidizing secondary products formed therefrom being performed by contact with transition metals or inorganic compounds thereof.

The process is of interest in particular for surfactant solutions which contain discolorations due to their preparation, which discolorations must be bleached to give light-colored products before use in formulations for the washing and cleaning sector, including personal care applications. This relates in particular, e.g. to alkyl polyglycosides.

Alkyl polyglycosides are prepared from natural raw materials and are non-toxic and readily degradable surface-active materials. They are therefore used as washing agents and cleaning agents and as emulsifiers and dispersers. However, they only have the desired surface-active properties when the alkyl groups have at least 8 C atoms. The alkyl polyglycosides in the context of this invention comply with the formula

$$R'-O-Z_n$$

in which R' represents a linear or branched, saturated or unsaturated aliphatic alkyl radical having 8 to 18 carbon atoms or mixtures thereof and $Z_n$ represents a polyglycosyl radical having an average value for n of 1.1 to 3 hexose or pentose units or mixtures thereof.

Preference is given to alkyl polyglycosides having alkyl radicals having 12 to 16 carbon atoms and having a polyglycosyl radical having an average value for n of 1.1 to 2. Particular preference is given to alkyl polyglycosides having a polyglycosyl radical having an average value for n of 1.1 to 1.4. The preferred polyglycosyl radical is the polyglycosyl radical.

2. Description of the Prior Art

Alkyl polyglycosides having long-chain alkyl groups are generally prepared by single-stage or multistage syntheses. A single-stage preparation process is described, inter alia, in DE-A-41 01 252.

A two-stage preparation process is specified, for example, in EP-A-0 306 652, according to which an n-butyl glycoside is first prepared by glycosidation with n-butanol and the desired long-chain alkyl polyglycoside is thereupon prepared by transglycosidation with a long-chain alcohol.

When the reaction is completed, the alkyl polyglycosides present are dissolved in long-chain alcohols. These alcohols must then be separated off if it is desired to obtain products which are completely soluble in water.

The aqueous alkyl polyglycoside solutions thus obtained are still too dark for high aesthetic requirements and must generally be subjected to a bleaching.

There are numerous references in the literature as to how the bleaching can be carried out. Thus, Staley (EP 0 165 721) describes a process for bleaching using hydrogen peroxide, sulphur dioxide, ozone or peracids. As no control or adjustment of the pH is provided, the bleaching results are unsatisfactory. Moreover, in this manner by-products can be formed to an undesired extent, some of which also have a pronounced inherent odor.

Other bleaching methods such as catalytic hydrogenation (U.S. Pat. No. 4,762,918, Staley), reaction with borohydride (EP 0 388 857, Kao) and irradiation with UV light (EP 0 526 710, Hüls) have proven to be insufficiently effective.

Bleaching in the presence of bleach boosters such as alkaline earth metal ions or alkali metal silicates (WO 93 13 113, Henkel) using hydrogen peroxide does give significantly better bleaching results but it is difficult to obtain products free from hydrogen peroxide under these conditions. Residual amounts of oxidizing agents must be avoided at any rate, since they effect inter alia the decomposition of additives in alkyl polyglycoside-containing formulations. The proposal to solve the problem of residual hydrogen peroxide bleaching in the presence of transition metal compounds (DE 42 18 073, Henkel) is likewise unconvincing. The then accelerated catalytic decomposition of hydrogen peroxide to give oxygen during the bleaching reaction decreases the available amount of hydrogen peroxide. The bleaching result is thus visibly impaired and made less effective.

The object was therefore to carry out the bleaching in such a way that in concentrated surfactant solutions after a first oxidative step the residual unreacted amount of hydrogen peroxide or oxidizing secondary products formed therefrom (e.g. peroxides) can be made harmless in a simple manner without intermediate removal of the stabilizer originally added.

SUMMARY OF THE INVENTION

It has now been found that an effective bleaching which leads to surfactant solutions free of hydrogen peroxide is possible if the process is carried out in two steps, in a first step the actual bleaching being performed using hydrogen peroxide and in a second step the residual peroxide decomposition and the decomposition of the oxidizing secondary products being performed using transition metals and compounds thereof in the presence of the stabilizer originally added.

The invention therefore relates to a process for bleaching aqueous, concentrated surfactant solutions, which is characterized in that in a first step the bleaching of the surfactant solutions is carried out in the presence of an inorganic hydrogen peroxide decomposition inhibitor and in a second step a specific decomposition of the unreacted hydrogen peroxide and/or oxidizing secondary products formed therefrom is performed in the presence of the decomposition inhibitor by transition metals and/or compounds thereof.

It is completely surprising in this context that the stabilizer activity of the decomposition inhibitors initially desired to carry out the first bleaching step does not lead to any inhibition of the decomposition in the second step and therefore in no way interferes with the decomposition of the undesired residual products and secondary products.

DESCRIPTION OF THE PREFERRED EMBODIMENTS

The first bleaching step, e.g. of an alkyl polyglycoside solution, is preferably performed continuously in a stirred reactor, in a tubular reactor or in a combination of stirred reactor and tubular reactor, the sequence being optional. However, a stirred-tank cascade can also be used. Discontinuous bleaching in the stirred reactor is also possible (batch mode).

In the bleaching the concentration of the aqueous alkyl polyglycoside solution is 30 to 75 per cent by weight. The amount of hydrogen peroxide used is 0.1 to 7, preferably 0.5 to 4, per cent by weight (based on dry matter). The temperature in the bleaching is 40° to 95° C., temperatures of 50° to 80° C. being particularly preferred. The pH is 7 to 12, preferably 8 to 11, and the concentration of stabilizer (decomposition inhibitor) is 50 to 10,000, preferably 200 to 6,000, ppm (based on dry matter). The hydrogen peroxide stabilizers used are preferably inorganic magnesium compounds.

The second step of the process, that is, the decomposition of residual amounts of hydrogen peroxide and/or oxidizing secondary products, is preferably performed continuously using transition metals and/or compounds thereof by passing the mass stream through a tubular reactor filled with a solid catalyst, if appropriate on a support. The catalyst can alternatively be added in the form of a metal salt solution, a stirred reactor being able to be used instead of a tubular reactor in this case.

Transition metals which can be used are chromium, manganese, iron, cobalt, nickel, copper, palladium or platinum and mixtures or alloys thereof. The transition metal compounds which can be used are salts of chromium, of manganese, of iron, of cobalt, of nickel, of copper, of palladium or of platinum and mixtures thereof.

Salts which are used are especially halides, sulphates, oxides and hydroxides of the metals mentioned.

Support materials for the transition metals or for water-insoluble transition metal compounds which are suitable are especially activated carbon, aluminum oxide and silicon dioxide.

The particle size in the fixed bed can be between 0.5 mm and 5 cm.

In addition to the use in pulverized form on support material, the metals can also be used e.g. as wire meshes, turnings, metal wool or sheet metal structures having a large surface area.

The temperature in the decomposition in the second step of the process is 20° to 150° C., preferably 30° to 120° C., the temperature range from 40° to 100° C. is particularly preferred.

The pH in the usual case is unchanged with respect to the first bleaching step. It is likewise 7 to 12, preferably 8 to 11. However, it can also if appropriate be readjusted within this range and therefore deviate from the pH of the first step.

The process has the following advantages:

the peroxide decomposition proceeds under mild conditions (no risk of product damage), the decomposition reaction is easy to control (no strong frothing due to excessive oxygen development at the beginning), short residence times are sufficient for complete peroxide decomposition under appropriate reaction conditions, very low-odor products are formed with extremely light color, the products are reliably free of hydrogen peroxide and peroxide, the products have high color stability on heating, the process is generally applicable to surfactant solutions which are dark-colored due to their preparation, e.g. solutions of anionic surfactants (examples: paraffinsulphonates, α-sulpho fatty acid methyl esters) and non-ionic surfactants (example: alkyl polyglycoside(s).

A continuous defoamer machine can be provided downstream of the first and/or second stage of the bleaching process, in which machine the alkyl polyglycoside(s) which is permeated by foam under some circumstances is compressed by centrifugation and is thus made more easily pumpable.

What is claimed as new and desired to be secured by Letters patent of the United States is:

1. A process for bleaching an aqueous, concentrated surfactant solution comprising
    (1) in a first step adding a bleaching composition to said solution to bleach said surfactant solution at an alkaline pH, wherein the composition comprises hydrogen peroxide in the presence of an inorganic hydrogen peroxide decomposition inhibitor, and
    (2) in a second subsequent step decomposing unreacted hydrogen peroxide and/or oxidizing secondary products formed therefrom in the presence of the decomposition inhibitor by the step consisting essentially of contacting the solution resulting from said first step with a transition metal and/or compound thereof.

2. A process for bleaching an aqueous, concentrated surfactant solution according to claim 1, wherein the surfactant is a non-ionic surfactant.

3. A process for bleaching an aqueous, concentrated surfactant solution according to claim 1, wherein the surfactant is an alkyl polyglycoside.

4. A process for bleaching an aqueous, concentrated surfactant solution according to claim 1, wherein the inhibitor comprises an inorganic magnesium compound.

5. A process for bleaching an aqueous, concentrated surfactant solution according to claim 1, wherein the transition metal is selected from the group consisting of chromium, manganese, iron, cobalt, nickel, copper, palladium, platinum, mixtures thereof, and alloys thereof.

6. A process for bleaching an aqueous, concentrated surfactant solution according to claim 1, wherein the transition metal compound is an inorganic salt of a metal selected from the group consisting of chromium, manganese, iron, cobalt, nickel, copper, palladium, platinum, and mixtures thereof.

7. A process for bleaching an aqueous, concentrated surfactant solution according to claim 1, wherein the transition metal and/or transition metal compound is supported by a support material selected from the group consisting of aluminum oxide, activated carbon and silicon dioxide.

8. A process for bleaching an aqueous, concentrated surfactant solution according to claim 1, wherein the decomposition is carried out at a temperature of 20° to 150° C.

9. A process for bleaching an aqueous, concentrated surfactant solution according to claim 1, wherein the pH is 7 to 12.

10. A process for bleaching an aqueous, concentrated surfactant solution according to claim 1, wherein the decomposition is performed in a tubular reactor.

* * * * *